(12) United States Patent
Lee et al.

(10) Patent No.: US 12,324,872 B2
(45) Date of Patent: Jun. 10, 2025

(54) ANTIMICROBIAL FILTER MEDIA, PREPARATION METHOD THEREOF, AND AIR CLEANER COMPRISING SAME

(71) Applicant: COWAY Co., Ltd., Gongju-si (KR)

(72) Inventors: Kyung Hwan Lee, Seoul (KR); Yoon Hyuck Choi, Seoul (KR); Jong Cheol Kim, Seoul (KR)

(73) Assignee: COWAY Co., Ltd., Gongju-si (KR)

( * ) Notice: Subject to any disclaimer, the term of this patent is extended or adjusted under 35 U.S.C. 154(b) by 478 days.

(21) Appl. No.: 17/877,059

(22) Filed: Jul. 29, 2022

(65) Prior Publication Data

US 2023/0085459 A1 Mar. 16, 2023

(30) Foreign Application Priority Data

Aug. 31, 2021 (KR) .................. 10-2021-0115984

(51) Int. Cl.
*A01N 43/78* (2006.01)
*A01N 59/26* (2006.01)
(Continued)

(52) U.S. Cl.
CPC .............. *A61L 9/014* (2013.01); *A01N 43/78* (2013.01); *A01N 59/26* (2013.01); *B01D 39/163* (2013.01); *B01D 39/2048* (2013.01); *B01D 46/0028* (2013.01); *B01J 20/048* (2013.01); *B01J 20/262* (2013.01); *B01J 20/28038* (2013.01); *B01J 20/3212* (2013.01); *B01J 20/3231* (2013.01); *B01J 20/3293* (2013.01); *A61L 2101/16* (2020.08); *A61L 2101/44* (2020.08); *A61L 2209/14* (2013.01); *B01D 2239/0442* (2013.01);
(Continued)

(58) Field of Classification Search
None
See application file for complete search history.

(56) References Cited

U.S. PATENT DOCUMENTS

2023/0243089 A1* 8/2023 Cesareo ................. B01D 39/08
427/359

FOREIGN PATENT DOCUMENTS

CN 111249812 A * 6/2020 ......... B01D 46/0001
KR 10-2010-0032659 A 3/2010

OTHER PUBLICATIONS

CN111249812A_ENG (Espacenet machine translation of Jin) (Year: 2020).*

* cited by examiner

*Primary Examiner* — Gabriel E Gitman
(74) *Attorney, Agent, or Firm* — Oblon, McClelland, Maier & Neustadt, L.L.P.

(57) ABSTRACT

An antimicrobial filter media, which includes a non-woven fabric; and an antimicrobial agent bound to the nonwoven fabric by a binder, the antimicrobial agent including silver sodium zirconium hydrogenphosphate and thiabendazole, and the silver sodium zirconium hydrogenphosphate and the thiabendazole are employed at a weight ratio of 1:1.5 to 1.5:1, to an air cleaner including the same, and to a process for preparing the same. The antimicrobial filter media includes silver sodium zirconium hydrogenphosphate and thiabendazole, as an antimicrobial agent, at a specific weight ratio. As a result, it is possible to effectively filter harmful microorganisms to supply purified air, to have excellent antibacterial, antiviral, and antifungal properties at the same time, and to further enhance the durability and lifespan characteristics by virtue of excellent filter damage prevention effect.

13 Claims, 2 Drawing Sheets

(51) Int. Cl.
  *A61L 9/014* (2006.01)
  *B01D 39/16* (2006.01)
  *B01D 39/20* (2006.01)
  *B01D 46/00* (2022.01)
  *B01J 20/04* (2006.01)
  *B01J 20/26* (2006.01)
  *B01J 20/28* (2006.01)
  *B01J 20/32* (2006.01)
  *A61L 101/16* (2006.01)
  *A61L 101/44* (2006.01)

(52) U.S. Cl.
  CPC ......... *B01D 2239/0492* (2013.01); *B01D 2239/0618* (2013.01); *B01D 2239/0627* (2013.01); *B01D 2239/10* (2013.01); *B01D 2279/65* (2013.01)

ANTIMICROBIAL FILTER MEDIA, PREPARATION METHOD THEREOF, AND AIR CLEANER COMPRISING SAME

TECHNICAL FIELD

The present invention relates to an antimicrobial filter media, to a process for preparing the same, and to an air cleaner comprising the same.

BACKGROUND ART

As air pollution problems such as fine dust and yellow dust have become serious in recent years, air purification that filters indoor air has become both desirable and essential. An air purifying device such as an air cleaner is capable of supplying fresh air is by filtering out contaminated dust or substances harmful to the human body in the air by using various filter systems.

In general, contaminants such as dust can be filtered by an air filter that primarily removes dust whereas microorganisms harmful to the human body such as mites, bacteria, mold, viruses, and the like are hardly filtered by a conventional air filter since they have a size of microns or less. Although a filter having micropores capable of filtering microorganisms having a size of microns or less may be additionally adopted, such a micropore filter has a problem in that filtered microorganisms proliferate on the surface of the filter media, which may be reintroduced into the room or generate unpleasant odors.

Therefore, there is a need for the development of an antimicrobial filter media that is capable of effectively filtering dust or microorganisms, is excellent in antibacterial, antiviral, and antifungal properties, thereby effectively preventing microorganisms harmful to the human body such as bacteria, mold, viruses, and the like from proliferating on the surface of the filter media, and is excellent in properties such as filter damage prevention effect, durability, and persistence of antibacterial and antifungal properties.

PRIOR ART DOCUMENT

Patent Document (Patent Document 1) Korean Laid-open Patent Publication No. 2010-0032659

DISCLOSURE OF INVENTION

Technical Problem

The present invention aims to provide an antimicrobial filter media that is capable of effectively filtering harmful microorganisms to thereby supply purified air, is excellent in antibacterial, antiviral, and antifungal properties, thereby effectively preventing microorganisms harmful to the human body such as bacteria, mold, viruses, and the like from proliferating on the surface of the filter media, and is excellent in properties such as filter damage prevention effect, durability, and persistence of antibacterial and antifungal properties, a process for preparing the same, and an air cleaner comprising the same.

Solution to Problem

The antimicrobial filter media according to an embodiment of the present invention comprises a non-woven fabric; and an antimicrobial agent bound to the nonwoven fabric by a binder, wherein the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

The process for preparing an antimicrobial filter media according to another embodiment of the present invention comprises unwinding a nonwoven fabric; immersing the nonwoven fabric in an antimicrobial composition; drying the immersed nonwoven fabric; and winding the dried nonwoven fabric, wherein the antimicrobial composition comprises an antimicrobial agent, a binder, and water, the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

The air cleaner according to still another embodiment of the present invention comprises the antimicrobial filter media.

Advantageous Effects of Invention

The antimicrobial filter media according to an embodiment of the present invention comprises a non-woven fabric; and an antimicrobial agent bound to the nonwoven fabric by a binder, wherein the antimicrobial agent comprises silver sodium zirconium hydrogenphosphate and thiabendazole, and they are employed at a specific weight ratio. As a result, it is possible to effectively filter harmful microorganisms to supply purified air, to have excellent antibacterial, antiviral, and antifungal properties at the same time, and to further enhance the durability, persistence of antibacterial and antifungal properties, and lifespan characteristics by virtue of excellent filter damage prevention effect.

BEST MODE FOR CARRYING OUT THE INVENTION

Hereinafter, the present invention is explained in detail. The present invention is not limited to the disclosures given below, but it may be modified into various forms as long as the gist of the invention is not changed.

Throughout the present specification, when a part is referred to as "comprising" an element, it is understood that other elements may be comprised, rather than other elements are excluded, unless specifically stated otherwise.

All numbers and expressions related to the quantities of components, reaction conditions, and the like used herein are to be understood as being modified by the term "about," unless otherwise indicated.

Throughout the present specification, the terms first, second, and the like are used to describe various components. But the components should not be limited by the terms. The terms are used only for the purpose of distinguishing one component from another.

In the present specification, in the case where each film, layer, or the like is mentioned to be formed "on" or "under" another film, layer, or the like, it means not only that one element is directly formed on or under another element, but also that one element is indirectly formed on or under another element with other element(s) interposed between them.

In addition, in the case where a component is referred to as being "connected," "supported," "introduced," "supplied," "flowing," or "bound" to another component, it should be understood that it may be directly connected, supported, introduced, supplied, flowing, or bound to another component, or an additional component may be present between them.

For the sake of description, the sizes of individual elements in the appended drawings may be exaggeratedly depicted, and they may differ from the actual sizes.

[Antimicrobial Filter Media]

The antimicrobial filter media according to an embodiment of the present invention comprises a non-woven fabric; and an antimicrobial agent bound to the nonwoven fabric by a binder, wherein the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

The antimicrobial filter media according to an embodiment of the present invention has excellent air permeability and serves as a filtering unit that can filter fine dust as well. Since it is possible to effectively prevent microorganisms harmful to the human body such as bacteria, mold, viruses, and the like from proliferating on the surface of the filter media, it has excellent antibacterial, antiviral, and antifungal properties at the same time and can further enhance the durability, persistence of antibacterial and antifungal properties, and lifespan characteristics by virtue of excellent filter damage prevention effect.

In particular, as the antimicrobial filter media comprises silver sodium zirconium hydrogenphosphate, it is very excellent in sterilization rate (antibacterial properties) and antiviral properties against microorganisms harmful to the human body such as *Staphylococcus aureus* and *Klebsiella pneumoniae*. And, as it comprises thiabendazole, it is very excellent in antifungal and antiviral properties against mold. In addition, as the antimicrobial filter media comprises silver sodium zirconium hydrogenphosphate and thiabendazole in a specific content range, it is excellent in antibacterial, antiviral, and antifungal properties and the persistence of these properties, and the durability and lifespan characteristics of the antimicrobial filter media may be further enhanced.

Specifically, the antimicrobial filter media may comprise the silver sodium zirconium hydrogenphosphate and the thiabendazole at a weight ratio of 1:1.5 to 1.5:1. For example, the weight ratio of the silver sodium zirconium hydrogenphosphate to the thiabendazole may be 1:1 to 1.5, greater than 1:1 to 1.5, or 1.5:1 to less than 1:1.

If the content of the silver sodium zirconium hydrogenphosphate is too small, the antibacterial properties may be deteriorated. If the content of the thiabendazole is too small, the antifungal properties may be deteriorated.

If the weight ratio of the silver sodium zirconium hydrogenphosphate to the thiabendazole satisfies the above range, the antimicrobial filter media may have excellent antibacterial, antiviral, and antifungal properties at the same time against microorganisms harmful to the human body.

Specifically, the antimicrobial filter media has a sterilization rate against *Staphylococcus aureus* and *Klebsiella pneumoniae* of, for example, greater than 99.99%, for example, 99.999% or more, for example, greater than 99.999%, for example, 100%, according to the test standard AATCC 100 test method. For example, the sterilization rate may be determined by, for example, placing a test specimen and a control group in a flask according to the shake flask method of KS J 4206:2008, injecting a test strain at about $10^5$, incubating it at about 35° C. for about 24 hours, and then collecting a sample in the flask and measuring the number of bacteria.

As the sterilization rate of the antimicrobial filter media against *Staphylococcus aureus* and *Klebsiella pneumoniae* satisfies the above range, the antimicrobial filter media has excellent sterilization properties and sterilization persistence.

In addition, the antimicrobial filter media may have a bacteria reduction rate of 95% or more as represented by the following Equation 1.

$$\text{Bacteria reduction rate} = \frac{BT1 - BT2}{BT1} \times 100 \qquad \text{[Equation 1]}$$

In Equation 1, BT1 is the number of bacteria after incubating the bacteria for 18 hours at 28±2° C. without the antimicrobial filter media, and BT2 is the number of bacteria after incubating the bacteria with the antimicrobial filter media under the same conditions.

Specifically, the bacteria reduction rate of the antimicrobial filter media according to Equation 1 may be 96% or more, 97% or more, 99% or more, 99.5% or more, or 99.9% or more. As the bacteria reduction rate of the antimicrobial filter media satisfies the above range, the antimicrobial filter media has excellent antibacterial properties and antibacterial persistence.

The bacteria reduction rate according to Equation 1 may be measured by the method stipulated in KS K 0693-2001.

Specifically, the bacteria reduction rate may be measured using *E. coli* (e.g., *Escherichia coli* NBRC 3301), but it is not limited thereto.

A strain is incubated using a nutrient media, and the number of viable bacteria is calculated by measuring the O.D. (optical density) value at 660 nm using an absorbance photometer. This is diluted with a nutrient media such that the initial number of bacteria has been adjusted, which may be used as an inoculum. The antimicrobial filter media is placed in a glass container with a lid, the inoculum is evenly sprayed, it is then incubated for 18 hours at 28±2° C., the number of bacteria is measured, and the bacteria reduction rate (%) is determined according to Equation 1.

In Equation 1, BT1 is the number of bacteria after incubating the bacteria for 18 hours at 28±2° C. without the antimicrobial filter media according to the present invention, which may stand for a control group. BT2 is the number of bacteria after incubating the bacteria with the antimicrobial filter media under the same conditions, which may stand for a test group.

In addition, the mold growth inhibition rate represented by the following Equation 2 may be 50% or more:

$$\text{Mold growth inhibition rate} = \frac{FG_2}{FM} \times 100 \quad \text{[Equation 2]}$$

In Equation 2, FM is the total area of the antimicrobial filter media in the form of a circular disk, and FG2 is the area of the mold growth inhibition section in the antimicrobial filter media when a mold spore solution of *Aspergillus niger* is applied to the antimicrobial filter media in the form of a circular disk and incubated for 2 weeks at 22° C. to 28° C. and a relative humidity of 50% or more in accordance with AATCC 30.

Specifically, the antimicrobial filter media may have a mold growth inhibition rate of, for example, 55% or more, for example, 60% or more, or, for example, 65% or more, as represented by Equation 2. As the mold growth inhibition rate of the antimicrobial filter media satisfies the above range, the antimicrobial filter media has excellent antifungal properties and antifungal persistence.

Meanwhile, the antimicrobial filter media according to an embodiment of the present invention may have a concentration variation ($\Delta M$) of Ag and Na in the antimicrobial filter media of 0.05 mg/L or less, respectively, as represented by the following Equation 3.

$$\Delta M(\text{mg/L}) = |M_0 - M_2| \quad \text{[Equation 3]}$$

In Equation 3, $M_0$ is the initial concentration (mg/L) of Ag or Na in the antimicrobial filter media, and $M_2$ is the concentration (mg/L) of Ag or Na in the antimicrobial filter media after continuous operation for 2 weeks at an operational flow rate of 5 m$^3$/minute under the conditions of a temperature of 20±5° C. and a humidity of 65±10%.

Specifically, when the concentration of Ag in the antimicrobial filter media is measured according to an embodiment of the present invention, that is, when $M_0$ in Equation 3 is the initial concentration (mg/L) of Ag in the antimicrobial filter media, and $M_2$ is the concentration (mg/L) of Ag in the antimicrobial filter media after continuous operation for 2 weeks at an operational flow rate of 5 m$^3$/minute under the conditions of a temperature of 20±5° C. and a humidity of 65±10%, the concentration variation ($\Delta M$) of Ag in the antimicrobial filter media may be, for example, 0.04 mg/L or less, for example, 0.03 mg/L or less, for example, 0.02 mg/L or less, for example, 0.01 mg/L or less, for example, 0.008 mg/L or less, for example, 0.005 mg/L or less, for example, 0.004 mg/L or less, or, for example, 0.003 mg/L or less.

In addition, when the concentration of Na in the antimicrobial filter media is measured according to an embodiment of the present invention, that is, when $M_0$ in Equation 3 is the initial concentration (mg/L) of Na in the antimicrobial filter media, and $M_2$ is the concentration (mg/L) of Na in the antimicrobial filter media after continuous operation for 2 weeks at an operational flow rate of 5 m$^3$/minute under the conditions of a temperature of 20±5° C. and a humidity of 65±10%, the concentration variation ($\Delta M$) of Na in the antimicrobial filter media may be, for example, 0.04 mg/L or less, for example, 0.03 mg/L or less, for example, 0.028 mg/L or less, for example, 0.025 mg/L or less, for example, 0.023 mg/L or less, for example, 0.02 mg/L or less, or, for example, 0.01 mg/L or less.

If the concentration variation ($\Delta M$) of Ag and Na in the antimicrobial filter media satisfies the above range, respectively, the reduction in the amount of antimicrobial agent is small, so that the antibacterial, antiviral, and antifungal properties may be persistently maintained, and the durability and lifespan characteristics of the antimicrobial filter media may be further enhanced.

In addition, after the antimicrobial filter media is subjected to continuous operation for 2 weeks at an operational flow rate of 5 m$^3$/minute under the conditions of a temperature of 20±5° C. and a humidity of 65±10%, the release amount ($\Delta CR$) of the antimicrobial agent remaining in the antimicrobial filter media as represented by the following Equation 4 may be 10 mg/L or less.

$$\Delta CR(\text{mg/L}) = |C_0 - C_2| \quad \text{[Equation 4]}$$

In Equation 4, $C_0$ is the initial concentration (mg/L) of the antimicrobial agent in the antimicrobial filter media, and $C_2$ is the concentration (mg/L) of the antimicrobial agent remaining in the antimicrobial filter media after continuous operation for 2 weeks at an operational flow rate of 5 m$^3$/minute under the conditions of a temperature of 20±5° C. and a humidity of 65±10%.

For example, the release amount of the antimicrobial agent may be 9 mg/L or less, 8.5 mg/L or less, 5 mg/L or less, 1 mg/L or less, 0.5 mg/L or less, 0.1 mg/L or less, 0.001 mg/L to 10 mg/L, 0.001 mg/L to 9 mg/L, 0.001 mg/L to 8.5 mg/L, 0.001 mg/L to 7.5 mg/L, 0.001 mg/L to 7 mg/L, 0.001 mg/L to 6 mg/L, 0.002 mg/L to 5 mg/L, 0.002 mg/L to 3 mg/L, 0.002 mg/L to 1 mg/L, 0.002 mg/L to 0.5 mg/L, 0.002 mg/L to 0.1 mg/L, or 0.002 mg/L to 0.06 mg/L.

In general, an organic material or an inorganic material may be applied in order to enhance the antimicrobial properties of a filter system. However, as such an organic or inorganic substance is released into the air, which causes a problem in that it is harmful to the human body. However, in the antimicrobial filter media according to an embodiment of the present invention, the release amount of silver sodium zirconium hydrogenphosphate and thiabendazole as an antimicrobial agent is very small, amounting to 10 mg/L or less; thus, its stability is very excellent, and the antibacterial, antiviral, and antifungal properties may be persistently maintained.

Due to the harmfulness of such a filter to the human body, the National Institute of Environmental Research has established a procedure for measuring the concentration of chemical substances in antimicrobial filters for air purification through the "Regulations on Standards and Methods for Testing and Inspection of Household Chemicals Subject to Safety Confirmation" (Ministry of Environment Notice No. 2019-45).

Specifically, the release amount of the antimicrobial agent may be measured by the method specified in the National Institute of Environmental Research Notice No. 2019-70.

More specifically, a sample of the antimicrobial filter media is sampled in a width of 30 cm and a length of 30 cm and mounted on a measuring device, it is subjected to continuous operation for 2 weeks at an operational flow rate of 5 m$^3$/minute under the conditions of a temperature of 20±5° C. and a humidity of 65±10%, and the release amount ($\Delta CR$) of the antimicrobial agent is calculated according to Equation 4. Here, five samples of the antimicrobial filter media are each subjected to the test for measuring the release amount, and an average value is calculated from the measured release amounts of the antimicrobial agent.

Meanwhile, the antimicrobial agent may be employed in an amount of 0.5% by weight to 5% by weight based on the total weight of the antimicrobial filter media. Specifically, the antimicrobial agent may be employed in an amount of, for example, 0.5% by weight to 3% by weight, for example, 0.5% by weight to 2% by weight, for example, 0.5% by weight to 1.5% by weight, for example, 0.5% by weight to 1.3% by weight, for example, 0.5% by weight to 1.25% by weight, for example, 1% by weight to 3% by weight, for example, 1% by weight to 2% by weight, or, for example, 1% by weight to 1.5% by weight, based on the total weight of the antimicrobial filter media.

If the antimicrobial agent may be employed in an amount within the above range based on the total weight of the antimicrobial filter media, it is possible to effectively prevent microorganisms harmful to the human body such as bacteria, mold, viruses, and the like from proliferating on the surface of the filter media; thus, it has excellent antibacterial, antiviral, and antifungal properties at the same time and can further enhance the durability and lifespan characteristics of the filter by virtue of excellent filter damage prevention effect.

Hereinafter, the components contained in the antimicrobial filter media according to an embodiment of the present invention will be described in detail.

Antimicrobial Agent
Silver Sodium Zirconium Hydrogenphosphate

According to an embodiment of the present invention, the antimicrobial filter media comprises silver sodium zirconium hydrogenphosphate.

The silver sodium zirconium hydrogenphosphate has a structure of the following Structural Formula 1 and produces the effect of further enhancing the sterilization rate, antibacterial effect, and antiviral effect as compared with other antimicrobial agents, which can inhibit contamination during the use of a filter.

[Structural Formula 1]

The silver sodium zirconium hydrogenphosphate may be employed in an amount of 0.2% by weight to 3.5% by weight based on the total weight of the antimicrobial filter media. For example, the content of the silver sodium zirconium hydrogenphosphate may be 0.2% by weight to 3.0% by weight, 0.2% by weight to 2.0% by weight, 0.2% by weight to 1.0% by weight, 0.25% by weight to 3.0% by weight, 0.25% by weight to 2.0% by weight, 0.25% by weight to 1.25% by weight, 0.4% by weight to 3.0% by weight, 0.4% by weight to 2.5% by weight, 0.4% by weight to 2.0% by weight, 0.4% by weight to 1.8% by weight, 0.4% by weight to 1.5% by weight, 0.4% by weight to 1.0% by weight, 0.4% by weight to 0.8% by weight, or 0.5% by weight to 0.75% by weight, based on the total weight of the antimicrobial filter media. As the content of the silver sodium zirconium hydrogenphosphate satisfies the above range, it is possible to effectively prevent microorganisms harmful to the human body such as bacteria, viruses, and the like from proliferating on the surface of the filter media; thus, it has excellent antibacterial properties and antiviral properties and further enhances the durability and lifespan characteristics of the filter by virtue of excellent filter damage prevention effect.

Thiabendazole

According to an embodiment of the present invention, the antimicrobial filter media comprises thiabendazole.

The thiabendazole has a structure of the following Structural Formula 2 and produces the effect of further enhancing antifungal and antiviral performance.

[Structural Formula 2]

The thiabendazole may be employed in an amount of 0.2% by weight to 3.5% by weight based on the total weight of the antimicrobial filter media. For example, the content of the thiabendazole may be 0.2% by weight to 3.0% by weight, 0.2% by weight to 2.0% by weight, 0.2% by weight to 1.0% by weight, 0.25% by weight to 3.0% by weight, 0.25% by weight to 2.0% by weight, 0.25% by weight to 1.25% by weight, 0.4% by weight to 3.0% by weight, 0.4% by weight to 2.5% by weight, 0.4% by weight to 2.0% by weight, 0.4% by weight to 1.8% by weight, 0.4% by weight to 1.5% by weight, 0.4% by weight to 1.0% by weight, 0.4% by weight to 0.8% by weight, or 0.5% by weight to 0.75% by weight, based on the total weight of the antimicrobial filter media. As the content of the thiabendazole satisfies the above range, it has excellent antifungal properties that inhibit the growth of mold, further enhances antiviral properties, and further enhances the durability and lifespan characteristics of the filter by virtue of excellent filter damage prevention effect.

Binder

According to an embodiment of the present invention, the antimicrobial filter media comprises a binder for binding the antimicrobial agent to a nonwoven fabric.

Specifically, the binder may comprise a urethane-based resin.

The binder binds the antimicrobial agent to a nonwoven fabric without a complicated process, thereby further enhancing the antibacterial, antiviral, and antifungal properties of the antimicrobial filter media.

As the antimicrobial filter media comprises a urethane-based resin, for example, a polyurethane binder as a binder, it is possible to enhance the rigidity and impact properties. Further, it may have excellent adhesion as compared with, for example, an acrylic binder.

In addition, the content of the binder may be 0.5% by weight to 5% by weight based on the total weight of the antimicrobial filter media. For example, the content of the binder may be 0.5% by weight to 4% by weight, 0.5% by weight to 3% by weight, or 0.5% by weight to 1% by weight, based on the total weight of the antimicrobial filter media. As the content of the binder satisfies the above range, the durability may be enhanced without deteriorating the air permeability.

The mixing weight ratio of the antimicrobial agent to the binder may be 1:10 to 10:1, 1:9 to 9:1, 1:8 to 8:1, 1:6 to 6:1, 1:5 to 5:1, 1:1 to 1.5:1, 1:1 to 1.25:1, or 1.25:0.5 to 0.75. If the mixing weight ratio of the antimicrobial agent to the binder satisfies the above range, the antimicrobial agent may be stably bound to a nonwoven fabric.

Nonwoven Fabric

According to an embodiment of the present invention, the antimicrobial filter media comprises a nonwoven fabric.

The nonwoven fabric may be a polyester-based nonwoven fabric. Specifically, it may comprise polyethylene terephthalate (PET). More specifically, it may comprise polyethylene terephthalate and rayon.

In addition, the content of the nonwoven fabric may be 40% by weight to 98% by weight based on the total weight of the antimicrobial filter media. For example, the content of the nonwoven fabric may be 45% by weight to 98% by weight, 45% by weight to 97% by weight, 50% by weight to 95% by weight, or 60% by weight to 95% by weight, based on the total weight of the antimicrobial filter media.

According to an embodiment of the present invention, the nonwoven fabric may comprise at least one selected from the group consisting of a polyester-based spunbond nonwoven fabric and a polyester-based thermalbond nonwoven fabric.

The spunbond nonwoven fabric is a nonwoven fabric made by extruding a polymer and stretching it to form a continuous filament, inserting the filament into a net, and heat-sealing, chemical bonding, or mechanical reinforcement by itself to form a filament net. For example, it may comprise a polyester-based spunbond nonwoven fabric. The basis weight of a spunbond layer comprising the spunbond nonwoven fabric may be 15 gsm to 80 gsm, 20 gsm to 60 gsm, or 20 gsm to 30 gsm.

If the nonwoven fabric comprises a polyester-based spunbond nonwoven fabric, the spunbond nonwoven fabric has a thin thickness, so that it may be advantageous for the purpose of antibacterial and antifungal treatment on the surface.

The thermalbond nonwoven fabric may comprise a polyester-based thermalbond nonwoven fabric. The basis weight of a thermalbond layer comprising the thermalbond nonwoven fabric may be 60 gsm to 90 gsm, 60 gsm to 80 gsm, 60 gsm to 70 gsm, 72 gsm to 90 gsm, 75 gsm to 80 gsm, or 85 gsm to 90 gsm.

If the thermalbond nonwoven fabric comprises a polyester-based thermalbond nonwoven fabric, the antimicrobial agent has excellent hygroscopicity, and it may be advantageous from the viewpoint of maintaining the rigidity of the filter media.

Meanwhile, according to an embodiment of the present invention, the nonwoven fabric may be a nonwoven fabric having a laminated structure comprising a first nonwoven fabric layer and a second nonwoven fabric layer. Specifically, the first nonwoven fabric layer and the second nonwoven fabric layer may each be a polyester-based nonwoven fabric. Specifically, they may each comprise polyethylene terephthalate (PET). More specifically, they may each comprise polyethylene terephthalate and rayon.

The first nonwoven fabric layer and the second nonwoven fabric layer may serve as a support layer. As the first nonwoven fabric layer and the second nonwoven fabric layer are laminated, the processability, handling convenience, and air permeability may be enhanced, and the dust collecting effect may be enhanced. The antimicrobial filter media according to an embodiment of the present invention comprises a nonwoven fabric comprising a first nonwoven fabric layer and a second nonwoven fabric layer, thereby preventing the antimicrobial filter media from being deformed by an external impact or during the manufacturing process or the use of the filter, and the processability and productivity may be enhanced.

The basis weight of the first nonwoven fabric layer may be 0 gsm to 60 gsm, greater than 0 gsm to 60 gsm, or 20 gsm to 30 gsm. The basis weight is measured as a gram per square meter, and it is a unit representing the weight of a fabric having an area of 1 m in width and 1 m in length. Thus, the larger the basis weight, the heavier or thicker the first nonwoven fabric layer. As the basis weight of the first nonwoven fabric layer satisfies the above range, the sustainability and bendability of the antimicrobial filter media may be enhanced, and the processability, in particular, workability at high temperatures may be enhanced.

In addition, the basis weight of the second nonwoven fabric layer may be 15 gsm to 50 gsm, for example, 20 gsm to 50 gsm, for example, 20 gsm to 30 gsm. As the basis weight of the second nonwoven fabric layer satisfies the above range, the sustainability and bendability of the antimicrobial filter media may be enhanced, and the processability, in particular, workability at high temperatures may be enhanced.

The sum of the basis weight of the first nonwoven fabric layer and the basis weight of the second nonwoven fabric layer may be 35 gsm to 85 gsm. For example, the sum of the basis weight of the first nonwoven fabric layer and the basis weight of the second nonwoven fabric layer may be 40 gsm to 80 gsm or 50 gsm to 80 gsm.

If the sum of the basis weight of the first nonwoven fabric layer and the basis weight of the second nonwoven fabric layer is less than 35 gsm, it has low durability and can be easily damaged such as tearing, and the bendability of the antimicrobial filter media may be deteriorated. In addition, if the sum of the basis weight of the first nonwoven fabric layer and the basis weight of the second nonwoven fabric layer exceeds 85 gsm, the bendability and processability may be deteriorated.

Pigment

According to an embodiment of the present invention, the antimicrobial filter media may further comprise a pigment. Specifically, as the antimicrobial filter media comprises a pigment, it is easy to distinguish the types of filters, and it is possible to prevent the contamination of the filter from being excessively emphasized, thereby preventing the problem that the user wrongly determines that the filter performance has been deteriorated.

The pigment may be an insoluble azo-based such as barium sulfate, calcium carbonate, titanium oxide, yellow iron oxide, black iron, chromium yellow, chromium familion, cadmium yellow, cadmium red, royal blue, ultramarine, and organic pigments; soluble azo-based; phthalocyaninebased; kinakryton-based; polyazo-based, or a mixture thereof. A green pigment such as Pigment Green and a yellow pigment such as Pigment Yellow may be preferable in that they can prevent misidentification of surface contamination of the filter, but it is not limited thereto.

In addition, the content of the pigment may be 0.2% by weight or less based on the total weight of the antimicrobial filter media. For example, the content of the pigment may be 0.2% by weight or less, less than 0.2% by weight, or 0.15% by weight or less, based on the total weight of the antimicrobial filter media.

[Process for Preparing an Antimicrobial Filter Media]

The process for preparing an antimicrobial filter media according to another embodiment of the present invention comprises unwinding a nonwoven fabric; immersing the nonwoven fabric in an antimicrobial composition; drying the immersed nonwoven fabric; and winding the dried nonwoven fabric, wherein the antimicrobial composition comprises an antimicrobial agent, a binder, and water, the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

Figure 1:
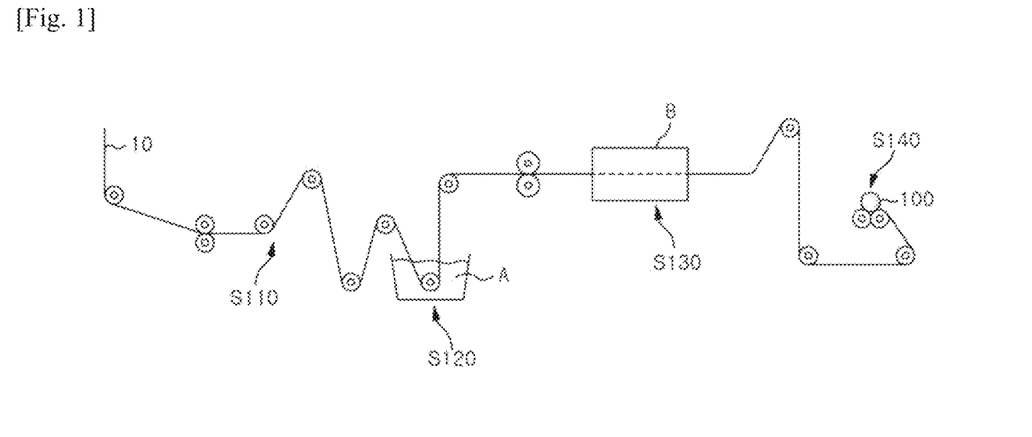
FIG. 1 schematically illustrates a process for preparing an antimicrobial filter media according to an embodiment of the present invention.
Figure 2:
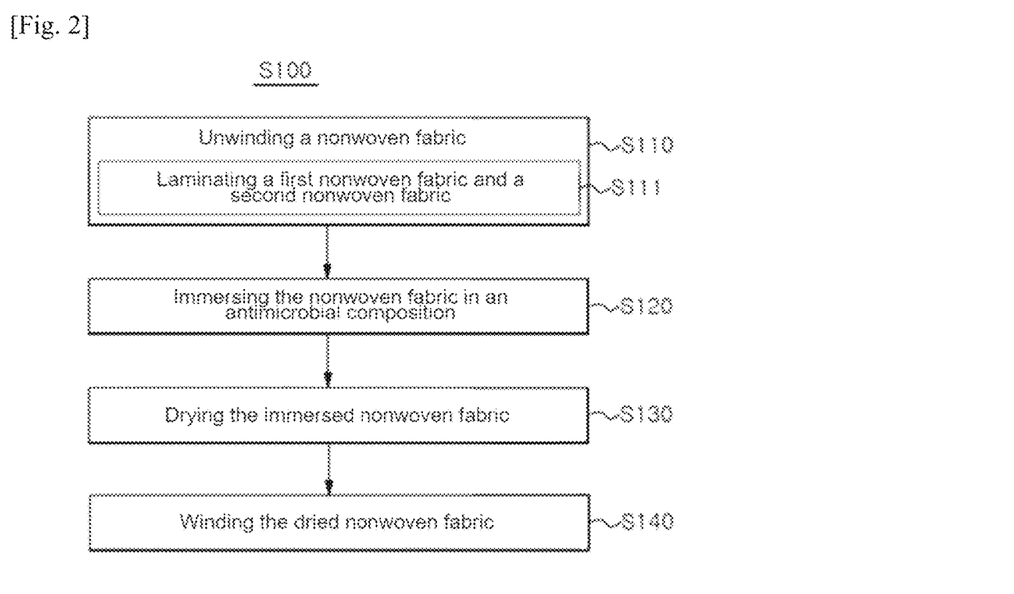
FIG. 2 is a flowchart illustrating a process for preparing an antimicrobial filter media according to an embodiment of the present invention.

FIG. 1 schematically illustrates a process for preparing an antimicrobial filter media according to an embodiment of the present invention. FIG. 2 is a flowchart (S100) illustrating a process for preparing an antimicrobial filter media according to an embodiment of the present invention.

The process for preparing an antimicrobial filter media according to an embodiment of the present invention may be carried out by, for example, a roll-to-roll process.

Referring to FIGS. 1 and 2 together, the process for preparing an antimicrobial filter media (100) comprises unwinding a nonwoven fabric (30) (S110).

Specifically, the step of unwinding a nonwoven fabric (S110) is carried out by a roll-to-roll process and for homogeneously forming a composition on the nonwoven fabric in a subsequent immersion step.

In addition, the process for preparing an antimicrobial filter media according to an embodiment of the present invention may further comprise laminating a first nonwoven fabric and a second nonwoven fabric (S111) before the unwinding step (S110).

Specifically, in the unwinding step (S110), the nonwoven fabric (30) prepared by laminating a first nonwoven fabric and a second nonwoven fabric may be unwound.

Details on the nonwoven fabric are as described above. In addition, the first nonwoven fabric and the second nonwoven fabric may be the same as the first nonwoven fabric layer and the second nonwoven fabric layer as described above, respectively, in terms of the components and properties.

The lamination step (S111) may be carried out at a temperature of 60° C. to 90° C. For example, the lamination step (S111) may be carried out at 70° C. to 90° C., 75° C. to 90° C., 75° C. to 85° C., or 78° C. to 85° C.

The lamination step (S111) may be carried out using a hot melt adhesive. Specifically, the lamination step (S111) may be carried out using a hot melt adhesive in an amount of 1 gsm to 10 gsm, 2 gsm to 10 gsm, or 3 gsm to 8 gsm. As the content of the hot melt adhesive satisfies the above range, the adhesiveness can be enhanced without deteriorating the air permeability.

The process for preparing an antimicrobial filter media (100) comprises immersing the nonwoven fabric in an antimicrobial composition (S120).

Specifically, the immersion step (S120) may be carried out by preparing an antimicrobial composition (A) comprising an antimicrobial agent comprising silver sodium zirconium hydrogenphosphate and thiabendazole and a binder and immersing the nonwoven fabric in the antimicrobial composition (A).

The antimicrobial composition (A) may comprise the antimicrobial agent in an amount of 5% by weight to 25% by weight, 10% by weight to 25% by weight, 5% by weight to 10% by weight, 10% by weight to 25% by weight, 15% by weight to 25% by weight, or 20% by weight to 25% by weight, based on the total weight of the antimicrobial composition.

For example, the antimicrobial composition (A) may comprise 5% by weight to 15% by weight of silver sodium zirconium hydrogenphosphate and 5% by weight to 15% by weight of thiabendazole based on the total weight of the antimicrobial composition. More specifically, the antimicrobial composition (A) may comprise 5% by weight to 15% by weight or 10% by weight to 15% by weight of silver sodium zirconium hydrogenphosphate and 5% by weight to 10% by weight of thiabendazole.

As the content of the antimicrobial agent satisfies the above range, the content of the antimicrobial agent in the antimicrobial filter media finally prepared may be adjusted to 0.5% by weight to 5% by weight. In addition, the antimicrobial filter media may comprise the silver sodium zirconium hydrogenphosphate and the thiabendazole at a weight ratio of 1:1.5 to 1.5:1. As a result, it is possible to enhance all of the antibacterial, antiviral, and antifungal properties. Details on the antimicrobial agent are as described above.

The antimicrobial composition (A) may comprise 5% by weight to 25% by weight of a binder based on the total weight of the antimicrobial composition.

For example, the antimicrobial composition (A) may comprise the binder in an amount of 10% by weight to 25% by weight, 10% by weight to 20% by weight, 10% by weight to 15% by weight, 12% by weight to 18% by weight, or 20% by weight to 25% by weight, based on the total weight of the antimicrobial composition.

As the content of the binder satisfies the above range, the content of the binder in the antimicrobial filter media finally prepared may be adjusted to 0.5% by weight to 5% by weight. Accordingly, the durability can be enhanced without deteriorating the air permeability of the antimicrobial filter media finally prepared. The binder may be the same as the binder described above in terms of the components and properties.

In addition, as the contents of the antimicrobial agent and the binder satisfy the above ranges, the dispersibility of the antimicrobial agent can be enhanced, resulting in an excellent quality of the antibacterial filter media.

The antimicrobial composition (A) may comprise 50% by weight to 80% by weight of a solvent based on the total weight of the antimicrobial composition. For example, the content of the solvent may be 60% by weight to 75% by weight, 60% by weight to 70% by weight, 60% by weight to 65% by weight, or 65% by weight to 70% by weight, based on the total weight of the antimicrobial filter media. The solvent may be purified water, but it is not limited thereto.

For example, the antimicrobial composition may further comprise 0.001% by weight to 0.2% by weight of a pigment, 0.01% by weight to 0.5% by weight of a surfactant, 0.001% by weight to 0.5% by weight of a dispersant, and the balanced amount of a solvent, based on the total weight of the antimicrobial composition.

Meanwhile, the immersion step (S120) may be carried out at 20° C. to 60° C. for 0.5 second to 3 seconds. For example, the immersion step (S120) may be carried out at 20° C. to 60° C., 30° C. to 60° C., 40° C. to 60° C., 30° C. to 50° C., 40° C. to 50° C., 20° C. to 35° C., or 22° C. to 32° C. for 1 second to 3 seconds, 0.5 second to 2 seconds, 0.5 second to 1.5 seconds, or 1 second to 2 seconds.

As the immersion step (S120) is carried out at a temperature and time described above, the antimicrobial agent can be uniformly dispersed, thereby enhancing the quality.

The process for preparing an antimicrobial filter media (100) comprises drying the immersed nonwoven fabric (S130).

Specifically, the drying step (S130) may be carried out at 80° C. to 150° C. at 14 mm/minute to 20 mm/minute. For example, the drying step (S130) may be carried out at 80° C. to 130° C., 100° C. to 150° C., 130° C. to 150° C., or 90° C. to 140° C. at 14 mm/minute to 18 mm/minute or 16 mm/minute to 20 mm/minute.

The drying step (S130) may be carried out using a drying device (B). For example, the drying device (B) may be a heater by hot air.

The process for preparing an antimicrobial filter media (100) comprises winding the dried nonwoven fabric (S140).

Specifically, the dried nonwoven fabric may be wound to prepare an antimicrobial filter media.

[Dust Collecting Filter]

The dust collecting filter according to still another embodiment of the present invention comprises the antimicrobial filter media, wherein the antimicrobial filter media comprises a non-woven fabric; and an antimicrobial agent bound to the nonwoven fabric by a binder, the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

The dust collecting filter may be formed by bending the antimicrobial filter media.

Specifically, the dust collecting filter may comprise a housing and a bent filter media disposed inside the housing.

The housing may serve as a frame for supporting the filter media. It may be assembled or molded such that the filter media may be properly disposed and mounted. The shape or structure of the housing may be arbitrarily determined according to the purpose of use or environment.

The material of the housing may be a material of a conventional housing used for a dust collecting filter. Specifically, at least one selected from the group consisting of an acrylonitrile-butadiene-styrene copolymer (ABS), polypropylene (PP), paper, nonwoven fabrics, polycarbonate (PC), and elastomer resins may be used as a material of the housing.

More specifically, ABS or PP may be used as the material of the housing, and ABS may be preferably used in consideration of the fact that dimensional accuracy may be readily secured and deformation during use may be suppressed. In addition, polyethylene terephthalate (PET) and ABS have high adhesion to each other. Thus, when PET is used for the antimicrobial filter media, and ABS is used for the housing, the prevention of delamination of the antimicrobial filter media and the housing may be enhanced.

The antimicrobial filter media may be disposed inside the housing by molding. Details on the antimicrobial filter media are as described above.

According to an embodiment of the present invention, the antimicrobial filter media may be bent to be disposed inside the housing. Specifically, the antimicrobial filter media may have a structure in which pleats are formed by bending. The shape of the pleats may vary, such as a zigzag type angular pleat or rounded pleat. The shape and size of the pleats are not particularly limited.

If the antimicrobial filter media is formed as bent in a dust collecting filter, the filtration area is wide to reduce the pressure loss and increase the life span of the filter. In addition, if the filter media is formed as bent in a dust collecting filter, the structure is firm, which enhances the durability and lifespan characteristics.

[Air Cleaner]

The air cleaner according to still another embodiment of the present invention comprises the antimicrobial filter media. Specifically, the air cleaner may comprise a dust collecting filter comprising the antimicrobial filter media.

The air cleaner according to still another embodiment of the present invention comprises an inlet for introducing polluted air; an outlet for discharging purified air; and a filter unit disposed between the inlet and the outlet, wherein the filter unit comprises an antimicrobial filter media, the antimicrobial filter media comprises a non-woven fabric; and an antimicrobial agent bound to the nonwoven fabric by a binder, the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

Details on the antimicrobial filter media are as described above. In addition, the air cleaner may comprise a dust collecting filter comprising the antimicrobial filter media. Details on the dust collecting filter are as described above.

Specifically, the air cleaner may be provided with an inlet in the front for introducing indoor air, an outlet formed at the upper part for discharging purified air, and a filter unit comprising the air purifying filter inside thereof.

In addition, the air cleaner may be provided with a blower fan that introduces indoor air by a rotational force and discharges purified air into the room. The blower fan introduces air through the front inlet and discharges it through the upper outlet. The outlet is provided with an outlet grill having a dense grid shape. As a result, it is possible to prevent the user's body from being injured by the rotating blower fan.

The filter unit may further comprise an additional filter in addition to the antimicrobial filter media or a dust collecting filter comprising the same. For example, it may further comprise a pre-filter for removing relatively large dust, mold, hair, pet hair, and the like and/or a dehumidifying filter having a plurality of pores to remove moisture in the air.

MODE FOR THE INVENTION

Hereinafter, the present invention will be described in more detail with reference to the following examples. However, these examples are set forth to illustrate the present invention, and the scope of the present invention is not limited thereto.

EXAMPLE

Preparation of an Antimicrobial Composition

Preparation Example 1

10% by weight of an antimicrobial agent comprising silver sodium zirconium hydrogenphosphate (CAS #265647-11-8) and thiabendazole (CAS #148-79-8) at a weight ratio of 5:5, 15% by weight of a urethane-based resin as a binder (polyurethane binder), and 75% by weight of purified water as a solvent were mixed to prepare an antimicrobial composition.

Preparation Examples 2 to 4

Antimicrobial compositions were each prepared in the same manner as in Preparation Example 1, except that the contents of components were changed as shown in Table 1 below.

TABLE 1

| Each component of the composition | Antimicrobial agent | | | | | |
|---|---|---|---|---|---|---|
| | Silver sodium zirconium hydrogenphosphate: thiabendazole (wt. ratio) | Silver sodium zirconium hydrogenphosphate (wt. %) | Thiabendazole (wt. %) | Antimicrobial agent content (wt. %) | Binder (wt. %) | Solvent (wt. %) |
| Prep. Ex. 1 | 1:1 | 5 | 5 | 10 | 15 | 75 |
| Prep. Ex. 2 | 1:1 | 10 | 10 | 20 | 15 | 65 |
| Prep. Ex. 3 | 1.5:1 | 15 | 10 | 25 | 15 | 60 |
| Prep. Ex. 4 | 1:1.5 | 10 | 15 | 25 | 10 | 65 |

Manufacture of an Antimicrobial Filter Media

Example 1

A polyester-based spunbond nonwoven fabric was unwound and then immersed in the antimicrobial composition of Preparation Example 1 at about 50° C. for about 2 seconds. Thereafter, the immersed nonwoven fabric was dried at about 140° C. at about 16 mm/minute using a hot air heater, and the dried nonwoven fabric was then wound to prepare an antimicrobial filter media.

Example 2

An antimicrobial filter media was prepared in the same manner as in Example 1, except that the antimicrobial composition of Preparation Example 2 was used.

Example 3

An antimicrobial filter media was prepared in the same manner as in Example 1, except that the antimicrobial composition of Preparation Example 3 was used.

Example 4

An antimicrobial filter media was prepared in the same manner as in Example 1, except that the antimicrobial composition of Preparation Example 4 was used.

The content of each component contained in the antimicrobial filter media prepared according to the above Examples is summarized in Table 2 below.

Specifically, a test specimen and a control group were each placed in a flask according to the shake flask method of KS J 4206:2008, a test strain was injected at about $10^5$, it was incubated at about 35° C. for about 24 hours, a sample in the flask was then collected, and the number of bacteria was measured. Here, the test specimen was a sample of the antimicrobial filter media of Examples 1 to 4 in a size of 4×4 mm FIG. 3 is a graph showing the sterilization rate (%) of the antimicrobial filter media of Examples 1 to 4 with respect to the mixing ratio of an antimicrobial agent.

Figure 3:
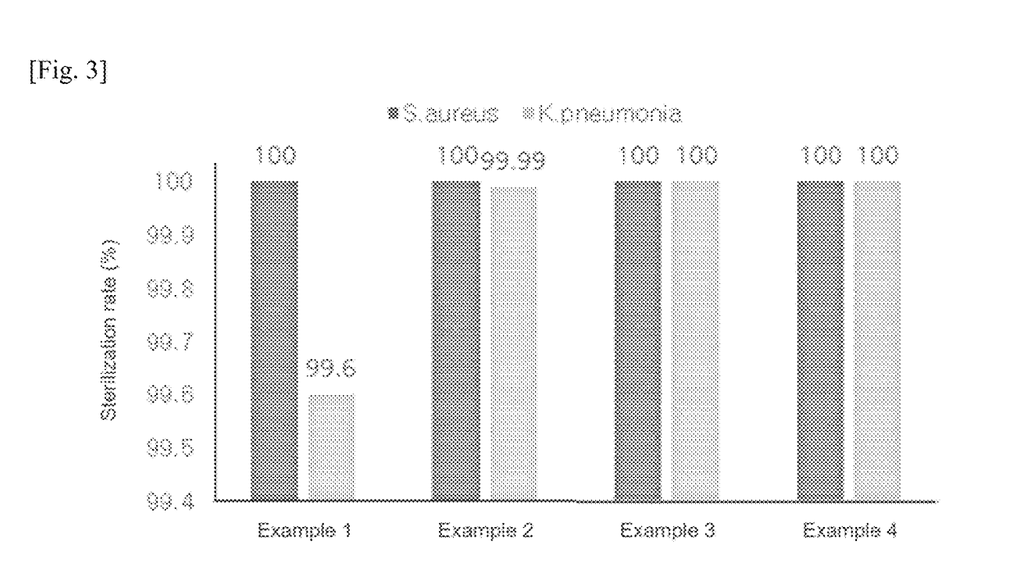
FIG. 3 is a graph showing the sterilization rate (%) of the antimicrobial filter media of Examples 1 to 4 with respect to the mixing ratio of an antimicrobial agent.
Figure 4:
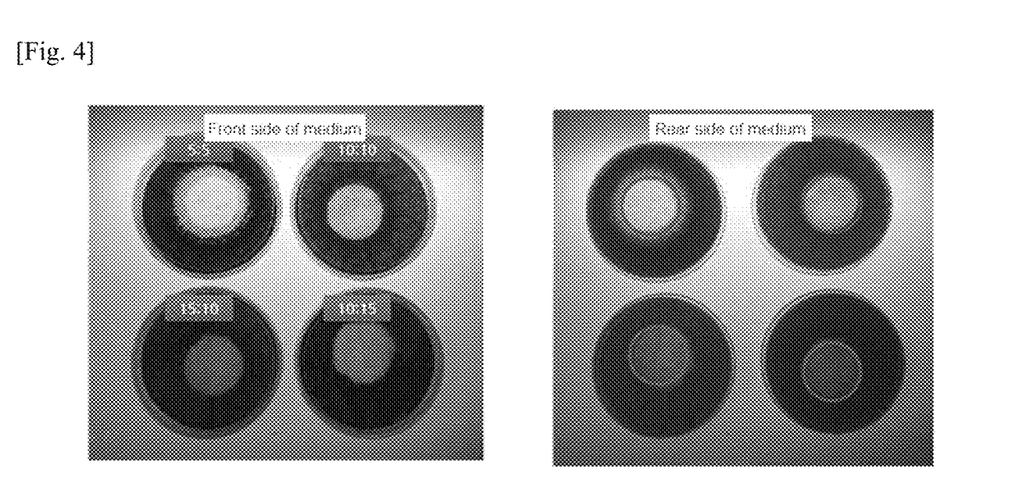
FIG. 4 is a photograph showing the results of an antifungal test of the antimicrobial filter media of Examples 1 to 4 with respect to the mixing ratio of an antimicrobial agent.

As can be seen from FIG. 3, all the antimicrobial filter media of Examples 1 to 4 had a sterilization rate of 100% against *Staphylococcus aureus*. In particular, the antimicrobial filter media of Examples 3 and 4 in which the antimicrobial agent comprising silver sodium zirconium hydrogenphosphate and thiabendazole at 1.5:1 and 1:1.5 had a sterilization rate of 100% against both *Staphylococcus aureus* and *Klebsiella pneumoniae*, confirming very excellent sterilization properties.

Test Example 2: Bacteria Reduction Rate

The antimicrobial filter media of the Examples were each subjected to a test for antibacterial properties according to the method specified in KS K 0693-2001. The strain, media, and reagent used are as follows.

1. Strain used: *E. coli* (*Escherichia coli* NBRC 3301)
2. Media and reagent

Nutrient Media 5 g of peptone (BACTO-Peptone Ehsms Thiotone) and 3 g of beef extract were dissolved in 1,000 ml of distilled

TABLE 2

| Each component of the antimicrobial filter media | Antimicrobial agent | | | | |
|---|---|---|---|---|---|
| | Silver sodium zirconium hydrogenphosphate:thiabendazole (wt. ratio) | Silver sodium zirconium hydrogenphosphate (wt. %) | Thiabendazole (wt. %) | Antimicrobial agent content (wt. %) | Binder (wt. %) |
| Prep. Ex. 1 | 1:1 | 0.25 | 0.25 | 0.5 | 0.75 |
| Prep. Ex. 2 | 1:1 | 0.5 | 0.5 | 1 | 0.75 |
| Prep. Ex. 3 | 1.5:1 | 0.75 | 0.5 | 1.25 | 0.75 |
| Prep. Ex. 4 | 1:1.5 | 0.5 | 0.75 | 1.25 | 0.5 |

TEST EXAMPLE

Test Example 1: Sterilization Rate

The sterilization rates against *Staphylococcus aureus* and *Klebsiella pneumoniae* were measured according to the test standard AATCC 100 test method.

water, its pH was adjusted to 6.8±0.2 (25° C.) with 0.1 M NaOH, and it was sterilized in an autoclave at a vapor pressure of 1,055 g/cm$^2$ and a temperature of 120±2° C. for 20 minutes.

Physiological Saline 5 g of NaCl was dissolved in 1,000 ml of distilled water, and it was sterilized in an autoclave at a vapor pressure of 1,055 g/cm$^2$ and a temperature of 120±2° C. for 20 minutes.

Neutralization Solution 5 g of NaCl and 2 g of a surfactant (Tween 80) were dissolved in 1,000 ml of distilled water, and it was sterilized in an autoclave at a vapor pressure of 1,055 g/cm$^2$ and a temperature of 120±2° C. for 20 minutes.

First, 20 ml of the nutrient media was charged into an Erlenmeyer flask, and the strain was inoculated. It was then incubated at 37±1° C. for 20 hours. The number of viable bacteria in the incubated bacterial solution was calculated by measuring the O.D. (optical density) value at 660 nm using an absorbance photometer. This was diluted with a nutrient media such that the initial number of bacteria was adjusted to 3.0×10$^4$, 0.2 ml of which was used as an inoculum.

Thereafter, 0.4 g of the antimicrobial filter media of Example 1 was sampled.

The sample of the antimicrobial filter media of Example 1 was placed in a 30-ml glass container with a lid, the inoculum was evenly sprayed to the sample, it was then incubated for 18 hours at 28±2° C., the number of bacteria was measured, and the bacteria reduction rate (%) was determined according to Equation 1.

$$\text{Bacteria reduction rate} = \frac{BT1 - BT2}{BT1} \times 100 \quad \text{[Equation 1]}$$

In Equation 1, BT1 is the number of bacteria after incubating the bacteria for 18 hours at 28±2° C. without the antimicrobial filter media, and BT2 is the number of bacteria after incubating the bacteria with the antimicrobial filter media under the same conditions.

Test Example 3: Mold Growth Inhibition Rate

In order to check the antifungal properties of the antimicrobial filter media, the mold growth inhibition rate of the antimicrobial filter media was measured using the mold of *Aspergillus niger*.

Specifically, the area of the mold growth inhibition section in the antimicrobial filter media when a mold spore solution of *Aspergillus niger* was applied to the antimicrobial filter media in the form of a circular disk having a diameter of 40 mm and incubated for 2 weeks at 22° C. to 28° C. and a relative humidity of 50% or more in accordance with AATCC 30. The mold growth inhibition rate was evaluated, as follows.

Very strong (◎): visible to the naked eye

Intermediate (Δ): observable under a 50-magnification microscope

Not observed (x): not observed by a microscope

The results of Test Examples 2 and 3 are summarized in Table 3 below.

TABLE 3

| | Initial number of bacteria (pfu/ml) | Number of bacteria after 18 hours (pfu/ml) | Bacteria reduction rate | Mold growth inhibition rate |
|---|---|---|---|---|
| Example 1 | 850 | 0 | 100 | Very strong (◎) |

As shown in Table 3 above, the antimicrobial filter media of Example 1 was excellent in both antiviral and antifungal properties.

Test Example 4: Safety of the Antimicrobial Filter Media

Concentrations of Ag and Na in the Antimicrobial Filter Media

In order to evaluate the safety, the antimicrobial filter media of Examples 1 to 3 were each measured for the concentrations of Ag and Na in the antimicrobial filter media by the method specified in the National Institute of Environmental Research Notice No. 2019-70.

Specifically, the antimicrobial filter media of Examples 1 to 3 were each made to a sample in a width of 30 cm and a length of 30 cm, which was mounted on a measuring device. It was then subjected to continuous operation for 2 weeks at an operational flow rate of 5 m$^3$/minute under the conditions of a temperature of 20±5° C. and a humidity of 65±10%, and the concentration (mg/L) of Ag or Na in the antimicrobial filter media was measured. The concentration change (ΔM) of Ag or Na in the antimicrobial filter media was then calculated according to the following Equation 3. The concentrations of Ag and Na shown in Table 4 below are average values obtained by carrying out the above concentration measurement test for 5 samples of the antibacterial filter media.

$$\Delta M(\text{mg/L}) = |M_0 - M_2| \quad \text{[Equation 3]}$$

In Equation 3, $M_0$ is the initial concentration (mg/L) of Ag or Na in the antimicrobial filter media, and $M_2$ is the concentration (mg/L) of Ag or Na in the antimicrobial filter media after continuous operation for 2 weeks at an operational flow rate of 5 m$^3$/minute under the conditions of a temperature of 20±5° C. and a humidity of 65±10%.

Release Amount of an Antimicrobial Agent

The antimicrobial filter media of Examples 1 to 3 were each measured for the release amount of the antimicrobial agent by the method specified in the National Institute of Environmental Research Notice No. 2019-70.

Specifically, the antimicrobial filter media of Examples 1 to 3 were each made to a sample in a width of 30 cm and a length of 30 cm, which was mounted on a measuring device. It was then subjected to continuous operation for 2 weeks at an operational flow rate of 5 m$^3$/minute under the conditions of a temperature of 20±5° C. and a humidity of 65±10%, and the release amount (ΔCR) of the antimicrobial agent was calculated according to Equation 4

The release amount shown in Table 4 below is an average value obtained by carrying out the above release amount measurement test for 5 samples of the antibacterial filter media.

$$\Delta CR(\text{mg/L}) = |C_0 - C_2| \quad \text{[Equation 4]}$$

In Equation 4, $C_0$ is the initial concentration (mg/L) of the antimicrobial agent in the antimicrobial filter media, and $C_2$ is the concentration (mg/L) of the antimicrobial agent remaining in the antimicrobial filter media after continuous operation for 2 weeks at an operational flow rate of 5 m$^3$/minute under the conditions of a temperature of 20±5° C. and a humidity of 65±10%.

The results are summarized in Table 4 below.

TABLE 4

|  | Ag | | | Na | | | |
| --- | --- | --- | --- | --- | --- | --- | --- |
|  | Ag before use (mg/L) | Ag after use for 2 weeks (mg/L) | Concentration change of Ag | Na before use (mg/L) | Na after use for 2 weeks (mg/L) | Concentration change of Na | Release amount of an antimicrobial agent |
| Example 1 | 0.246 | 0.245 | 0.001 | 0.958 | 0.947 | 0.011 | 0.012 |
| Example 2 | 0.258 | 0.222 | 0.036 | 0.972 | 0.945 | 0.027 | 0.059 |
| Example 3 | 0.223 | 0.208 | 0.015 | 0.953 | 0.931 | 0.022 | 0.037 |

As can be seen from Table 4, the concentration change of Ag and the concentration change of Na in the antibacterial filter media of Examples 1 to 3 were very low, amounting to 0.036 mg/L or less and 0.027 mg/L or less, respectively. As a result, the reduction in the amount of the antimicrobial agent is small, so that the antibacterial, antiviral, and antifungal properties can be persistently maintained, and the durability and lifespan characteristics of the antimicrobial filter media can be further enhanced.

Meanwhile, the release amount of the antimicrobial agent remaining in the antibacterial filter media of Examples 1 to 3 was very low, amounting to 0.012 to 0.059 mg/L. As a result, the stability is very excellent, and the antibacterial, antiviral, and antifungal properties can be persistently maintained.

The invention claimed is:

1. An antimicrobial filter media, which comprises a nonwoven fabric; and an antimicrobial agent bound to the nonwoven fabric by a binder, wherein the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

2. The antimicrobial filter media of claim 1, which has a sterilization rate of greater than 99.99% against *Staphylococcus aureus* and *Klebsiella pneumoniae* according to the test standard AATCC 100 test method.

3. The antimicrobial filter media of claim 1, which has a bacteria reduction rate of 95% or more as represented by the following Equation 1:

$$\text{Bacteria reduction rate} = \frac{BT1 - BT2}{BT1} \times 100 \qquad \text{[Equation 1]}$$

in Equation 1, BT1 is the number of bacteria after incubating the bacteria for 18 hours at 28±2° C. without the antimicrobial filter media, and BT2 is the number of bacteria after incubating the bacteria with the antimicrobial filter media under the same conditions.

4. The antimicrobial filter media of claim 1, which has a concentration variation (ΔM) of Ag and Na in the antimicrobial filter media of 0.05 mg/L or less, respectively, as represented by the following Equation 3:

$$\Delta M(\text{mg/L}) = |M_0 - M_2| \qquad \text{[Equation 3]}$$

In Equation 3, $M_0$ is the initial concentration (mg/L) of Ag or Na in the antimicrobial filter media, and $M_2$ is the concentration (mg/L) of Ag or Na in the antimicrobial filter media after continuous operation for 2 weeks at an operational flow rate of 5 m³/minute under the conditions of a temperature of 20±5° C. and a humidity of 65±10%.

5. The antimicrobial filter media of claim 1, which has a release amount (ΔCR) of the antimicrobial agent remaining in the antimicrobial filter media of 10 mg/L or less as represented by the following Equation 4:

$$\Delta CR(\text{mg/L}) = |C_0 - C_2| \qquad \text{[Equation 4]}$$

In Equation 4, $C_0$ is the initial concentration (mg/L) of the antimicrobial agent in the antimicrobial filter media, and $C_2$ is the concentration (mg/L) of the antimicrobial agent remaining in the antimicrobial filter media after continuous operation for 2 weeks at an operational flow rate of 5 m³/minute under the conditions of a temperature of 20±5° C. and a humidity of 65±10%.

6. The antimicrobial filter media of claim 1, wherein the antimicrobial agent is employed in an amount of 0.5% by weight to 5% by weight based on the total weight of the antimicrobial filter media.

7. The antimicrobial filter media of claim 1, wherein the binder comprises a urethane-based resin, and the binder is employed in an amount of 0.5% by weight to 5% by weight based on the total weight of the antimicrobial filter media.

8. The antimicrobial filter media of claim 1, wherein the nonwoven fabric comprises at least one selected from the group consisting of a polyester-based spunbond nonwoven fabric and a polyester-based thermalbond nonwoven fabric.

9. An air cleaner, which comprises the antimicrobial filter media according to claim 1.

10. A process for preparing an antimicrobial filter media, which comprises:
unwinding a nonwoven fabric;
immersing the nonwoven fabric in an antimicrobial composition;
drying the immersed nonwoven fabric; and
winding the dried nonwoven fabric,
wherein the antimicrobial composition comprises an antimicrobial agent, a binder, and water, the antimicrobial agent comprises silver sodium zirconium hydrogenphosphate and thiabendazole, and the silver sodium zirconium hydrogenphosphate and the thiabendazole are employed at a weight ratio of 1:1.5 to 1.5:1.

11. The process for preparing an antimicrobial filter media of claim 10, wherein the immersion step is carried out at 20° C. to 60° C. for 0.5 second to 3 seconds, and the drying step is carried out at 80° C. to 150° C. at 14 mm/minute to 20 mm/minute.

12. The process for preparing an antimicrobial filter media of claim 10, wherein the antimicrobial agent is employed in an amount of 5% by weight to 25% by weight, and the binder is employed in an amount of 5% by weight to 25% by weight, based on the total weight of the antimicrobial composition.

13. The process for preparing an antimicrobial filter media of claim 12, wherein the antimicrobial composition further comprises 0.001% by weight to 0.2% by weight of a pigment, 0.01% by weight to 0.5% by weight of a surfactant, 0.001% by weight to 0.5% by weight of a dispersant, and the balanced amount of a solvent, based on the total weight of the antimicrobial composition.

* * * * *